United States Patent
Purdy et al.

(10) Patent No.: US 7,766,953 B2
(45) Date of Patent: Aug. 3, 2010

(54) DEPLOYMENT SYSTEM FOR AN EXPANDABLE STENT

(75) Inventors: James D. Purdy, Lafayette, IN (US); Joseph M. Stewart, IV, Delphi, IN (US)

(73) Assignee: Med Institute, Inc., West Lafayette, IN (US)

( * ) Notice: Subject to any disclaimer, the term of this patent is extended or adjusted under 35 U.S.C. 154(b) by 501 days.

(21) Appl. No.: 11/803,965

(22) Filed: May 16, 2007

(65) Prior Publication Data

US 2008/0288042 A1 Nov. 20, 2008

(51) Int. Cl.
A61F 2/06 (2006.01)
(52) U.S. Cl. .................................... 623/1.12
(58) Field of Classification Search .................. None
See application file for complete search history.

(56) References Cited

U.S. PATENT DOCUMENTS

| | | | |
|---|---|---|---|
| 5,026,377 A | 6/1991 | Burton et al. | |
| 5,201,757 A | 4/1993 | Heyn et al. | |
| 5,415,664 A | 5/1995 | Pinchuk | |
| 5,480,423 A | 1/1996 | Ravenscroft et al. | |
| 5,683,451 A * | 11/1997 | Lenker et al. | 623/1.11 |
| 5,690,644 A | 11/1997 | Yurek et al. | |
| 5,709,703 A * | 1/1998 | Lukic et al. | 623/1.12 |
| 5,824,041 A * | 10/1998 | Lenker et al. | 606/195 |
| 6,139,572 A | 10/2000 | Campbell et al. | |
| 6,251,132 B1 | 6/2001 | Ravenscroft et al. | |
| 6,346,118 B1 | 2/2002 | Baker et al. | |
| 6,350,278 B1 | 2/2002 | Lenker et al. | |
| 6,579,297 B2 | 6/2003 | Bicek et al. | |
| 6,656,212 B2 | 12/2003 | Ravenscroft et al. | |
| 6,849,084 B2 | 2/2005 | Rabkin et al. | |
| 6,858,034 B1 * | 2/2005 | Hijlkema et al. | 606/108 |
| 2001/0012944 A1 | 8/2001 | Bicek et al. | |
| 2003/0109886 A1 | 6/2003 | Keegan et al. | |
| 2004/0044395 A1 | 3/2004 | Nelson | |
| 2004/0049256 A1 | 3/2004 | Yee | |
| 2004/0093063 A1 | 5/2004 | Wright et al. | |
| 2004/0098079 A1 | 5/2004 | Hartley et al. | |
| 2004/0106974 A1 | 6/2004 | Greenberg et al. | |
| 2004/0133264 A1 | 7/2004 | Moore | |
| 2004/0230286 A1 | 11/2004 | Moore et al. | |
| 2005/0060018 A1 | 3/2005 | Dittman | |
| 2005/0085890 A1 | 4/2005 | Rasmussen et al. | |

(Continued)

*Primary Examiner*—Todd E Manahan
*Assistant Examiner*—Brian Graham
(74) *Attorney, Agent, or Firm*—Brinks Hofer Gilson & Lione

(57) ABSTRACT

A deployment system and method for an expandable stent are described. The deployment system includes an expandable stent in an unexpanded state and a first tubular sheath having one or more first flaps extending from a distal end thereof. The one or more first flaps overlie one or more first longitudinal portions of the stent. A second tubular sheath may overlie the first tubular sheath. The deployment method includes advancing a deployment system including an expandable stent in an unexpanded state to a treatment site in a body vessel. At the treatment site, one or more second longitudinal portions of the stent are radially expanded to partially deploy the stent, and then one or more first longitudinal portions of the stent are radially expanded to fully deploy the stent. Each of the first and second longitudinal portions preferably extends from a proximal end to a distal end of the stent.

13 Claims, 14 Drawing Sheets

U.S. PATENT DOCUMENTS

2005/0090887 A1 4/2005 Pryor
2005/0131514 A1 6/2005 Hijlkema et al.
2005/0288766 A1 12/2005 Plain et al.

* cited by examiner

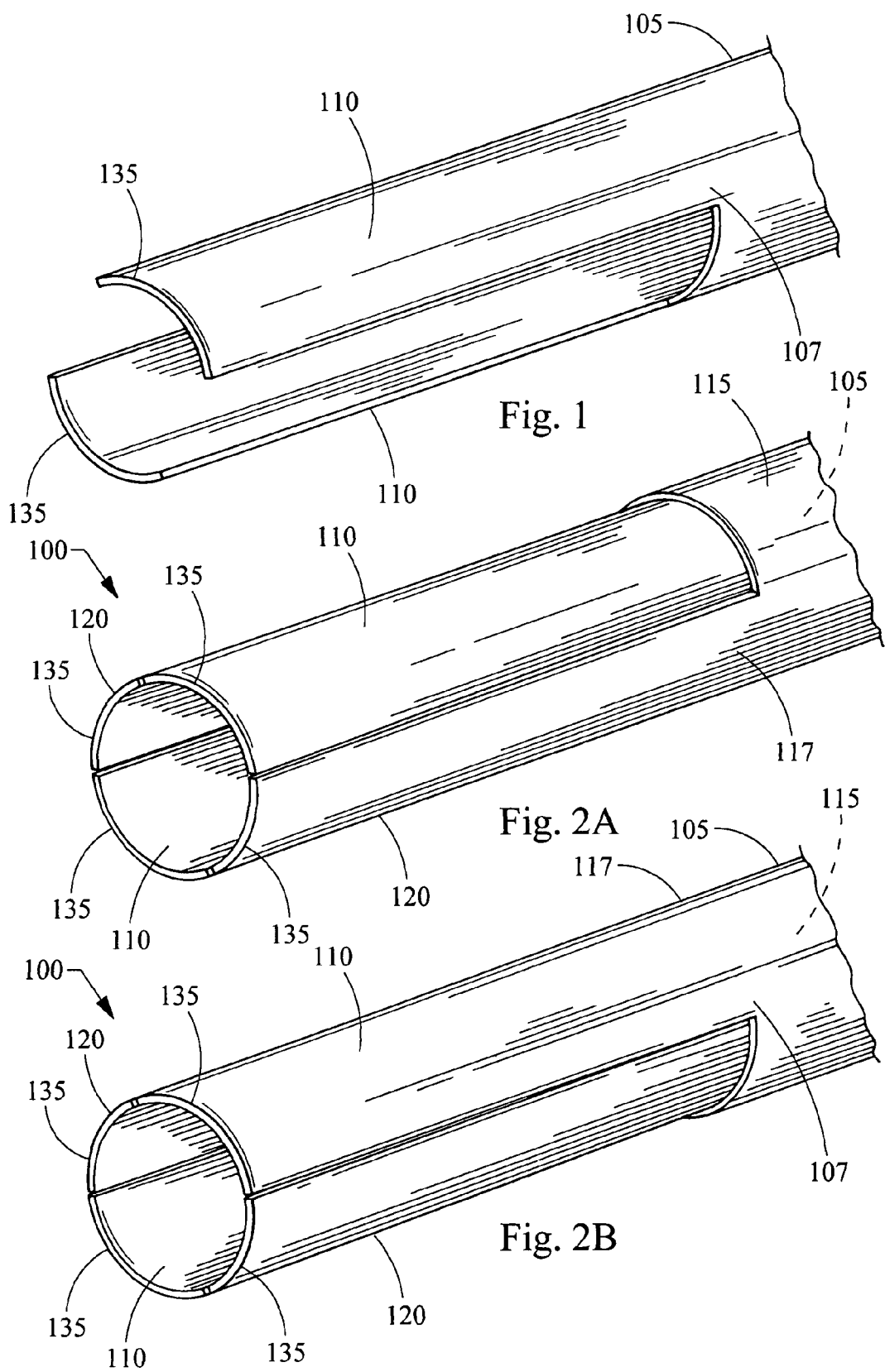

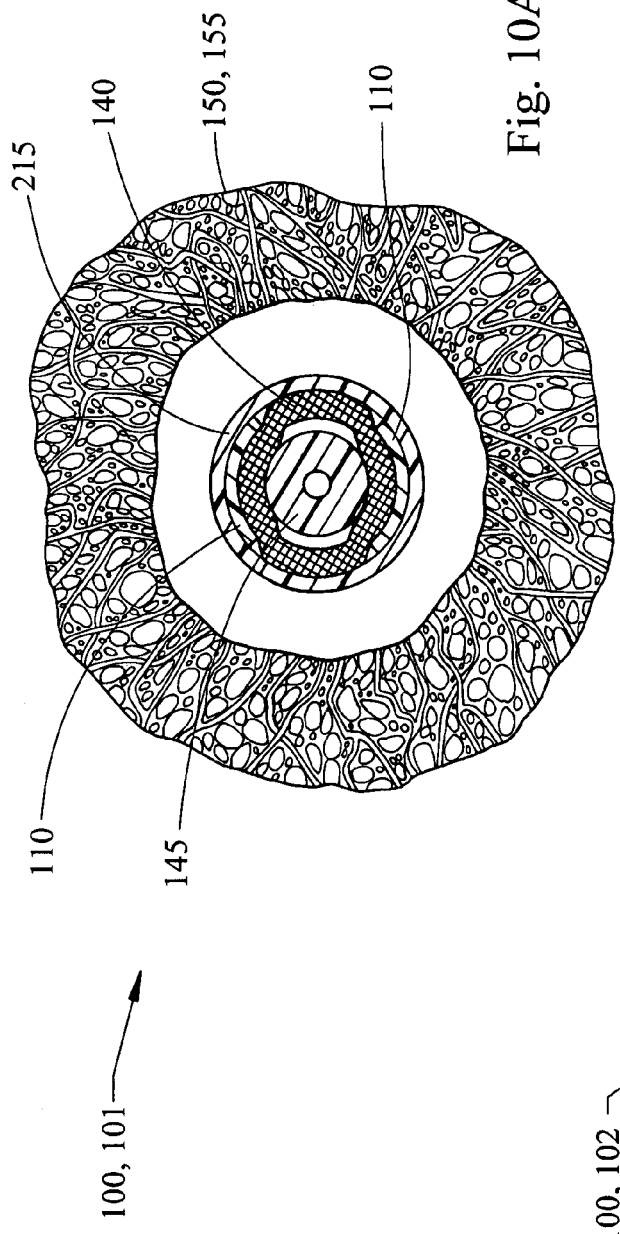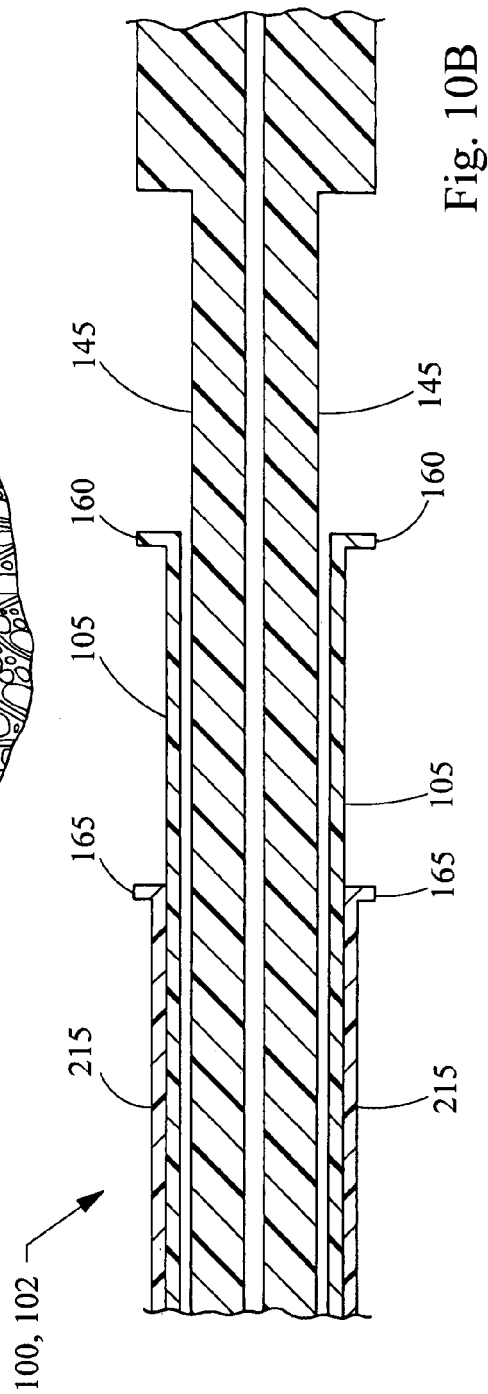

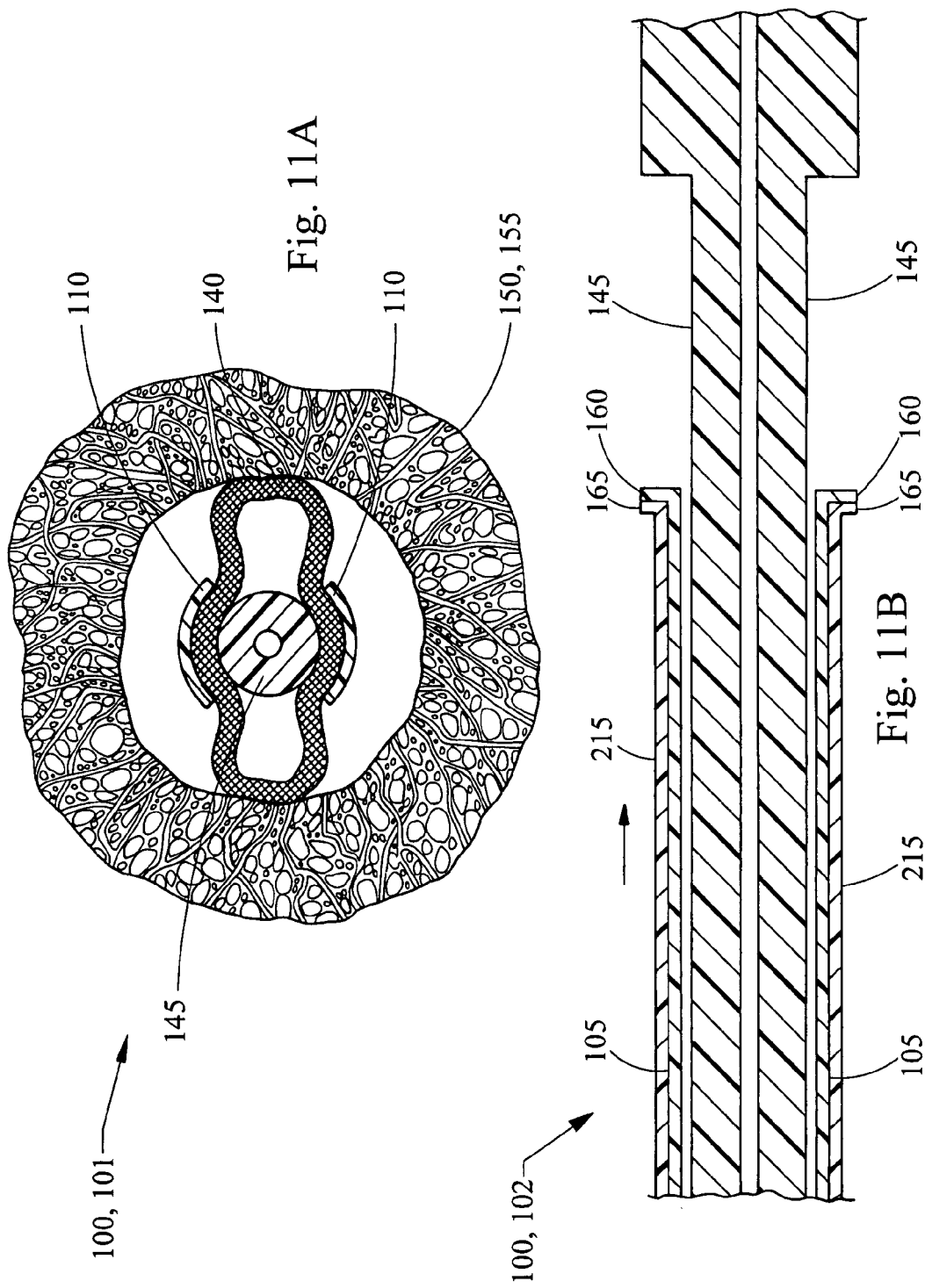

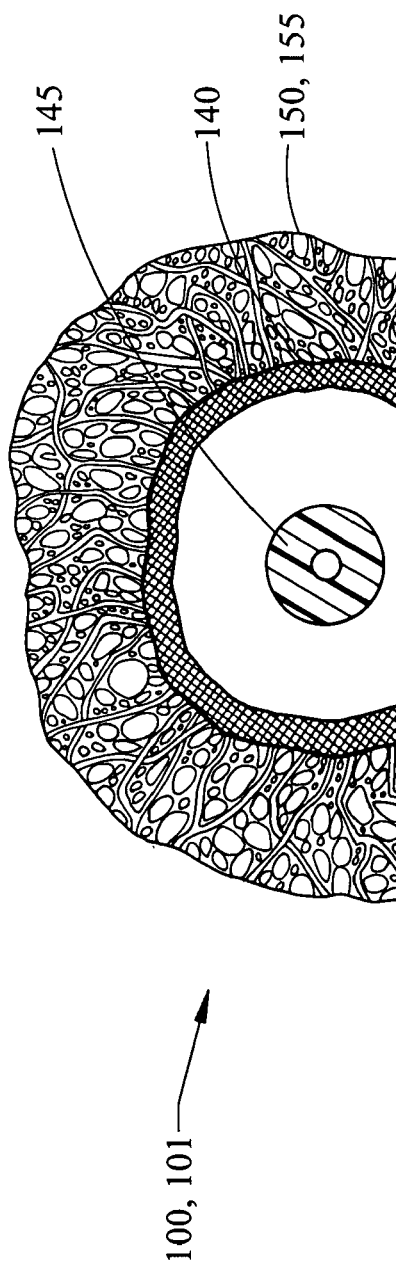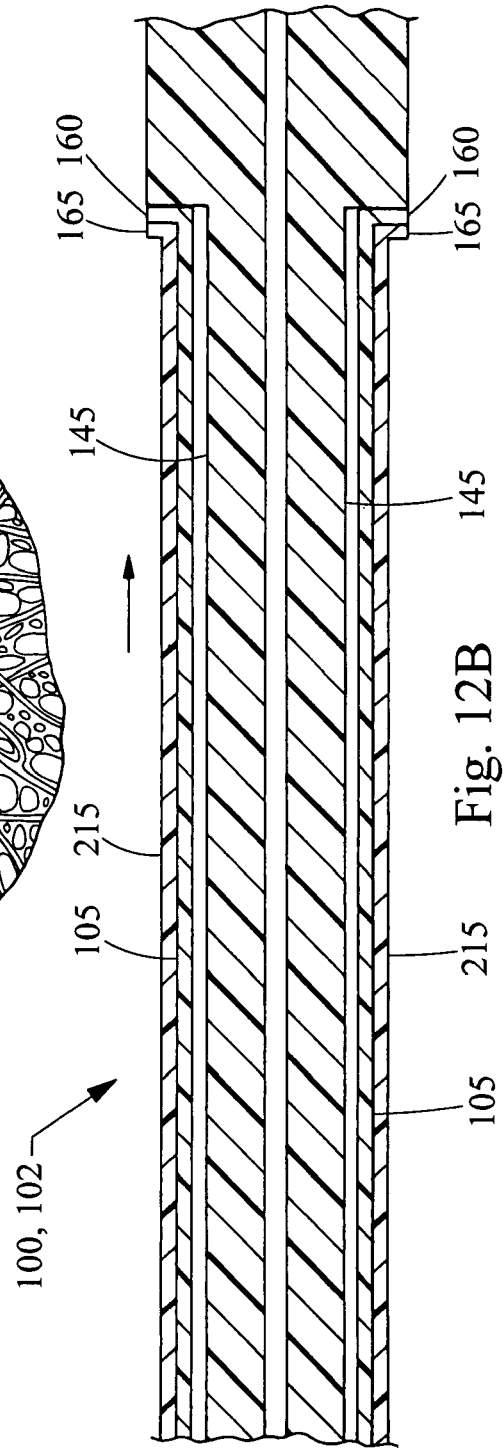

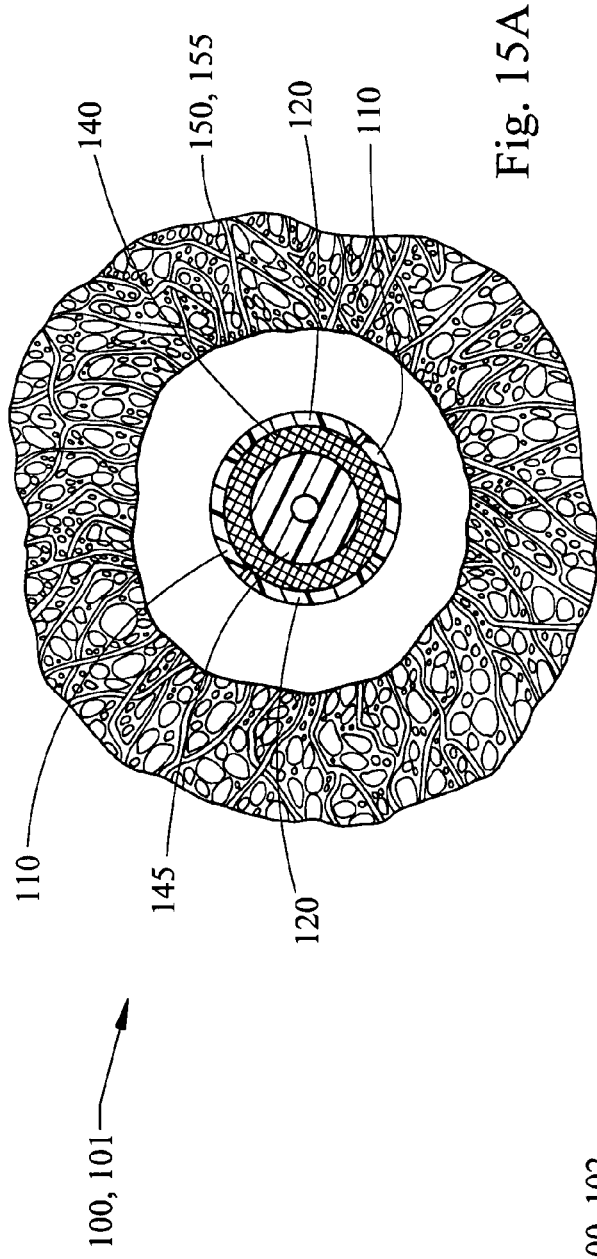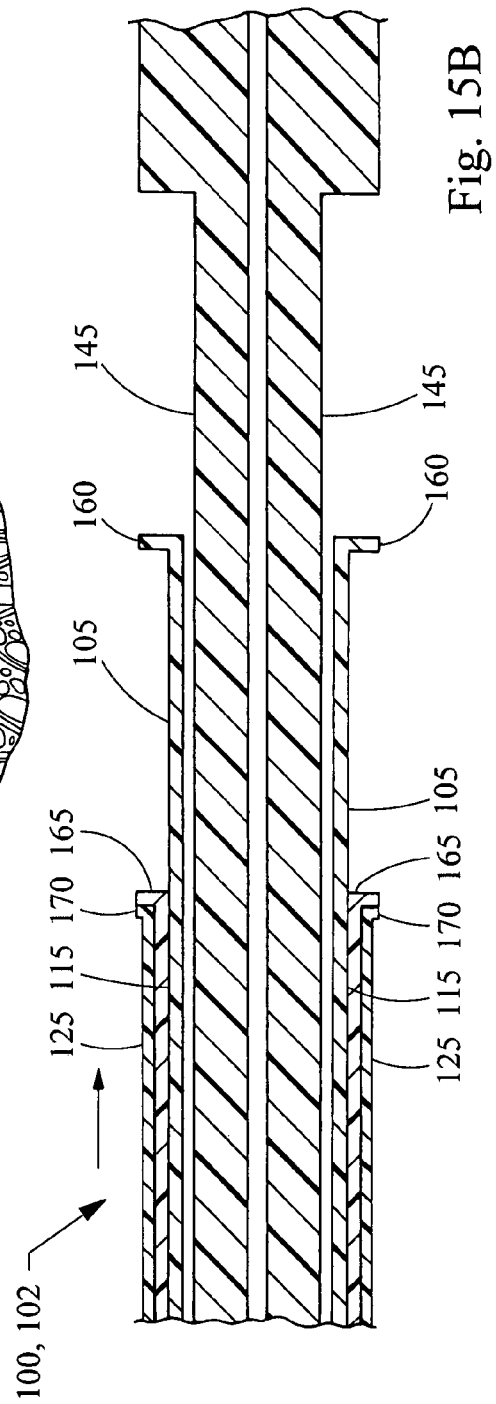

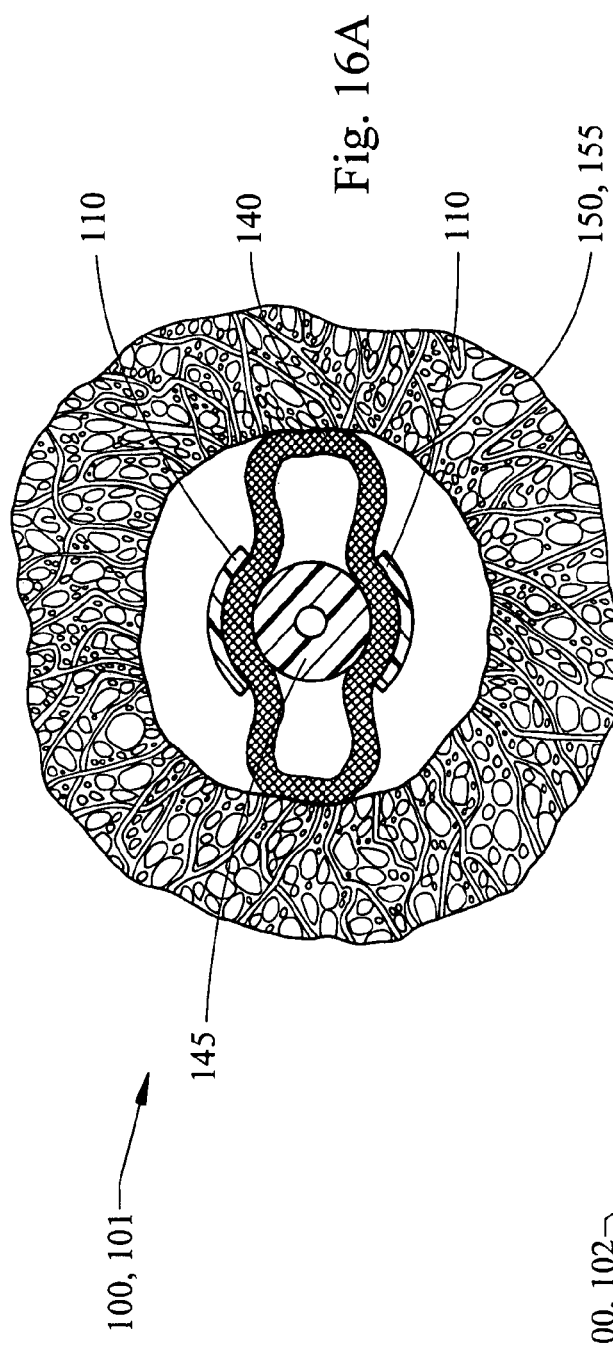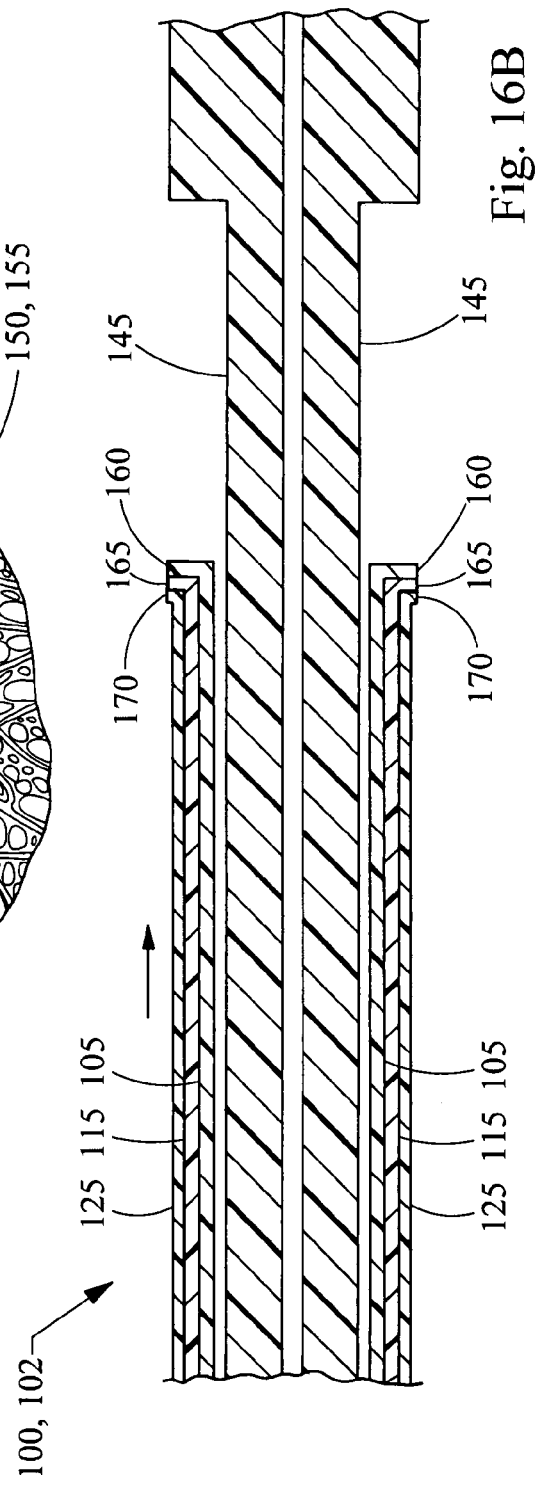

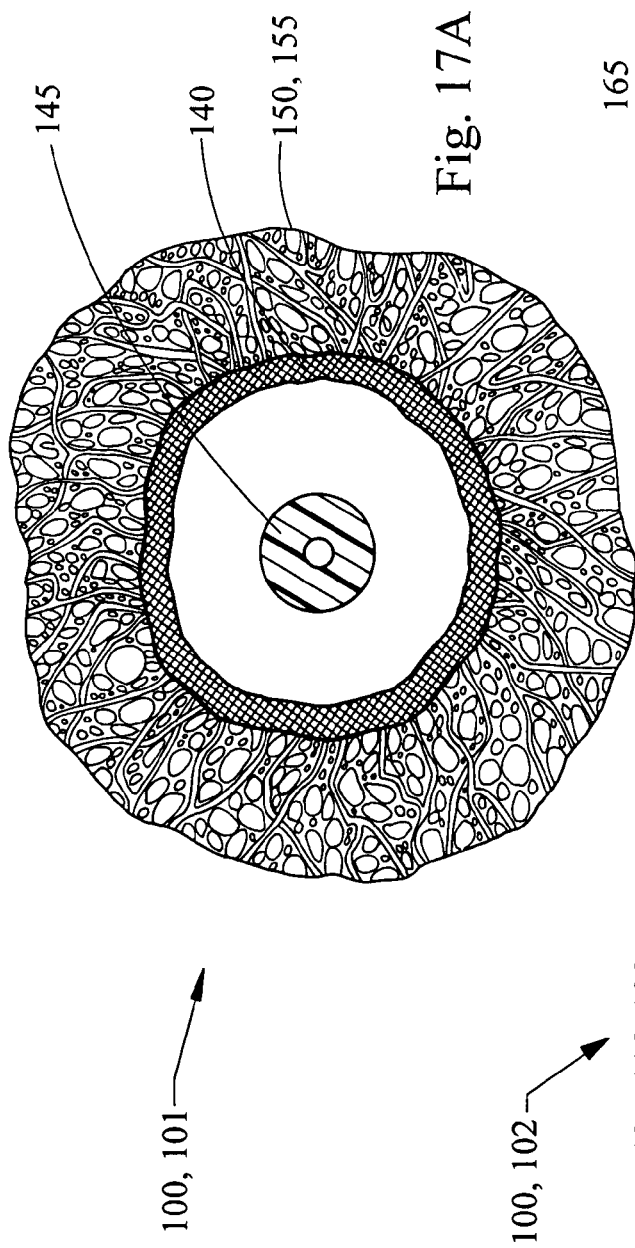
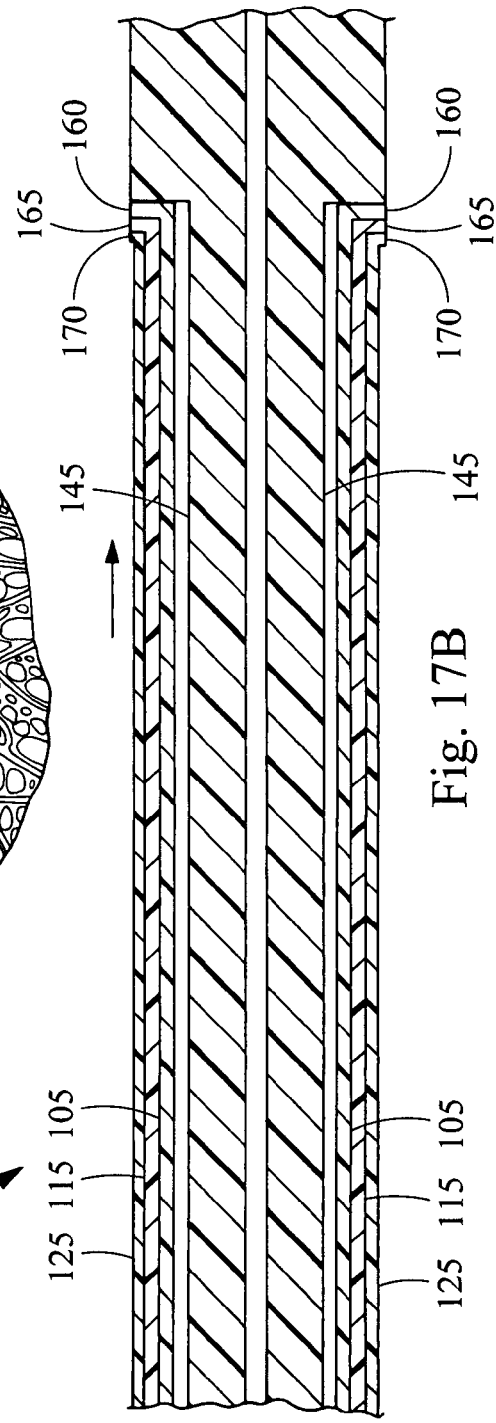

US 7,766,953 B2

DEPLOYMENT SYSTEM FOR AN EXPANDABLE STENT

TECHNICAL FIELD

The present disclosure is generally related to medical devices and, more particularly, to deployment systems for expandable stents.

BACKGROUND

Stents are generally designed as tubular support structures that can be used in a variety of medical procedures to treat blockages, occlusions, narrowing ailments and other problems that restrict flow through body vessels. Expandable stents are radially compressed for delivery within a vessel and then radially expanded once in place at a treatment site, where the tubular support structure of the stent contacts and supports the inner wall of the vessel. Expandable stents are generally classified as either balloon-expandable or self-expanding. Balloon-expandable stents expand in response to the inflation of a balloon, while self-expanding stents expand spontaneously when released from a delivery device.

Generally, to deliver a self-expanding stent or other intraluminal device into a vessel of interest, a hollow needle is used to penetrate the vessel and a wire guide is threaded through the needle and into the vessel. The needle is removed, and an introduction catheter is inserted over the wire guide. The stent is radially compressed to a low profile configuration and inserted into a tubular retaining sheath that prevents the stent from expanding during delivery. The stent and the sheath are directed through the introduction catheter and into the vessel. Once the stent reaches the treatment site, the sheath is retracted and the stent expands from its low profile configuration to an expanded state in which it exerts an outward radial force against the vessel wall.

During retraction of the sheath, the distal end of the stent typically expands first while the proximal end remains restrained by a distal portion of the sheath. Continued retraction of the sheath allows the remainder of the stent to be gradually released from the sheath. A problem may arise, however, due to friction between the inner wall of the sheath and the surface of the stent. Instead of sliding smoothly over the stent, the sheath may tend to grip the stent as it retracts, causing the stent to stretch, twist, or otherwise deform. Since the distal end of the stent is normally in contact with the vessel wall during the retraction, this deformation may in turn be transferred to the vessel. Axial elongation or twisting of the stent structure may also lead to inaccurate placement of the stent at the treatment site.

Accordingly, it is apparent to the inventors that an improved deployment system for an expandable stent would be advantageous.

BRIEF SUMMARY

A deployment system for an expandable stent is described herein. Also described is a method of deploying an expandable stent that may reduce or eliminate unwanted deformation of the stent as it expands to contact a body vessel.

The deployment system includes an expandable stent in an unexpanded state and a first tubular sheath having one or more first flaps extending from a distal end thereof. The one or more first flaps overlie one or more first longitudinal portions of the stent. The deployment system may further include a second tubular sheath overlying the first tubular sheath.

The method of deploying an expandable stent comprises advancing a deployment system including an expandable stent in an unexpanded state to a treatment site in a body vessel. At the treatment site, one or more second longitudinal portions of the stent are radially expanded to partially deploy the stent while one or more first longitudinal portions of the stent remain undeployed. Then, the one or more first longitudinal portions of the stent are radially expanded to fully deploy the stent at the treatment site. Each of the first and second longitudinal portions extends from a proximal end to a distal end of the stent.

BRIEF DESCRIPTION OF THE DRAWINGS

FIG. 1 is a perspective view of a portion of a tubular sheath including two flaps extending from a distal end thereof;

FIG. 2A is a perspective view of a portion of a deployment system according to one embodiment;

FIG. 2B is a perspective view of a portion of a deployment system according to another embodiment;

FIG. 10A is a cross-sectional view of the distal part of the deployment system shown in FIG. 9 taken along section 10A-10A;

FIG. 10B is a longitudinal cross-sectional view of a proximal part of the deployment system of FIG. 9 prior to deployment of the stent;

FIG. 11A is a cross-sectional view of the distal part of the deployment system shown in FIG. 9 following partial deployment of the stent;

FIG. 11B is a longitudinal cross-sectional view of the proximal part of the deployment system of FIG. 9 following partial deployment of the stent;

FIG. 12A is a cross-sectional view of the distal part of the deployment system shown in FIG. 9 following complete deployment of the stent;

FIG. 12B is a longitudinal cross-sectional view of the proximal part of the deployment system of FIG. 9 following complete deployment of the stent;

FIG. 15A is a cross-sectional view of the distal part of the deployment system shown in FIG. 13 following retraction of a third tubular sheath and prior to deployment of the stent;

FIG. 15B is a longitudinal cross-sectional view of a proximal part of the deployment system of FIG. 13 following retraction of the third tubular sheath and prior to deployment of the stent;

FIG. 16A is a cross-sectional view of the distal part of the deployment system shown in FIG. 13 following partial deployment of the stent;

FIG. 16B is a longitudinal cross-sectional view of the proximal part of the deployment system of FIG. 13 following partial deployment of the stent;

FIG. 17A is a cross-sectional view of the distal part of the deployment system shown in FIG. 13 following complete deployment of the stent; and FIG. 17B is a longitudinal cross-sectional view of the proximal part of the deployment system of FIG. 13 following complete deployment of the stent.

DETAILED DESCRIPTION

Figure 3:
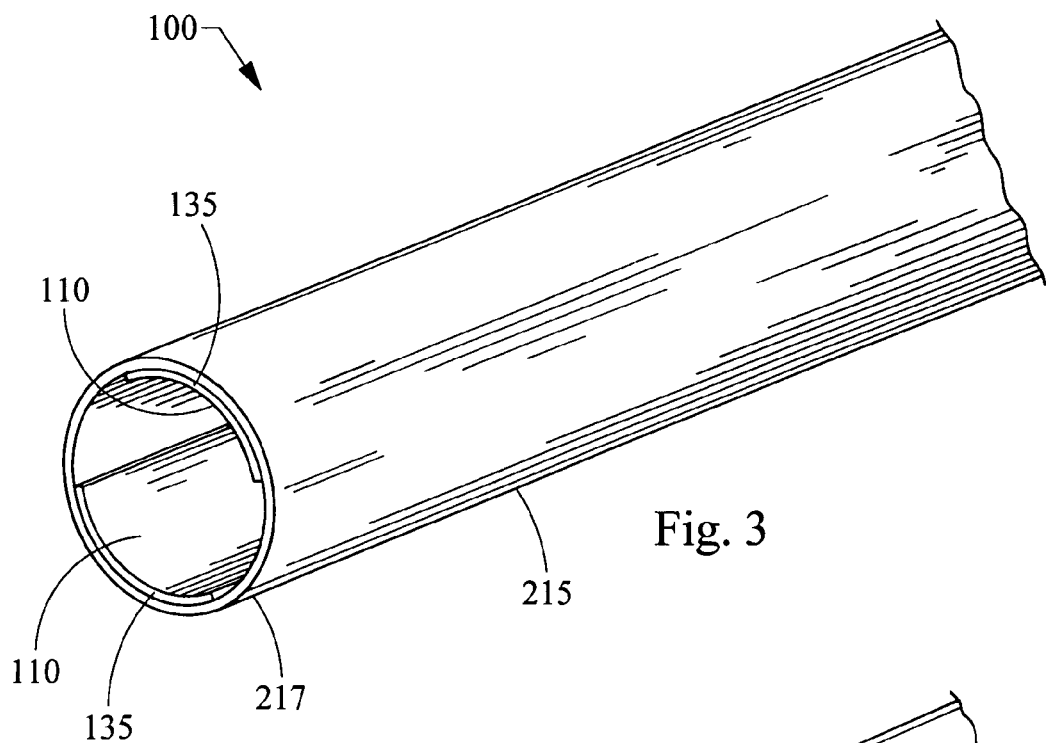
FIG. 3 is a perspective view of a portion of a deployment system according to another embodiment.

A deployment system for an expandable stent and a method of deploying a stent are described herein. The deployment system includes a tubular sheath having one or more flaps extending from a distal end thereof. The one or more flaps are configured to overlie one or more longitudinal portions of an expandable stent prior to deployment thereof. Each longitudinal portion may extend entirely from one end of the stent to the other, but only partway about a circumference of the stent. Accordingly, each flap preferably has a length at least as long as an entire length of the stent and a partially annular cross-section, i.e., a cross-section corresponding to a portion of a ring.

FIG. 1 shows a first tubular sheath 105 of the deployment system 100 according to one embodiment. Preferably, the first tubular sheath 105 has two longitudinal flaps 110 extending from the distal end 107. The flaps are configured to overlie two longitudinal portions of a stent prior to deployment of the portions. The one or more flaps 110 include a distal portion 135. According to this embodiment, the flaps 110 are disposed in opposition to each other and are symmetrically arranged about a circumference of the tubular sheath 105. Asymmetric arrangements of the flaps 110 are also possible. It is further contemplated that the first tubular sheath 105 may have one flap, three flaps, four flaps, or more than four flaps extending from the distal end 107, depending on the particular deployment characteristics desired.

Preferably, the deployment system 100 also includes a second tubular sheath 115 disposed coaxially with the first tubular sheath 105. The second tubular sheath 115 may overlie the first tubular sheath 105, as shown in FIG. 2A. Alternatively, as shown in FIG. 2B, the first tubular sheath 105 may overlie the second tubular sheath 115.

The second tubular sheath 115 may have one or more flaps 120 extending from a distal end 117 thereof. Again referring to FIGS. 2A and 2B, the second tubular sheath 115 preferably has two flaps 120 extending from the distal end 117 of the second tubular sheath 115. The flaps 120 are configured to overlie one or more longitudinal portions of the stent not covered by the flaps 110 of the first tubular sheath 105. The one or more flaps 120 include a distal portion 135. According to this embodiment, the flaps 120 are disposed in opposition to each other and are symmetrically arranged about a circumference of the second tubular sheath 115. Asymmetric arrangements of the flaps 120 are also possible. It is further contemplated that the second tubular sheath 115 may have one flap, three flaps, four flaps, or more than four flaps extending from the distal end 117 as desired. Preferably, the flaps 120 of the second tubular sheath 115 are disposed alternately with the flaps 110 of the first tubular sheath 105 about a circumference of the deployment system 100.

According to an alternative embodiment, as shown in FIG. 3, the second tubular sheath 215 may not include the one or more flaps 120. According to this embodiment, the second tubular sheath 215 overlies the first tubular sheath 105 and at least a proximal portion of the flaps 110 extending from the distal end 107 of the first tubular sheath 105. A distal portion 217 of the second tubular sheath 215 overlying the flaps 110 has an annular cross-section.

Figure 4:
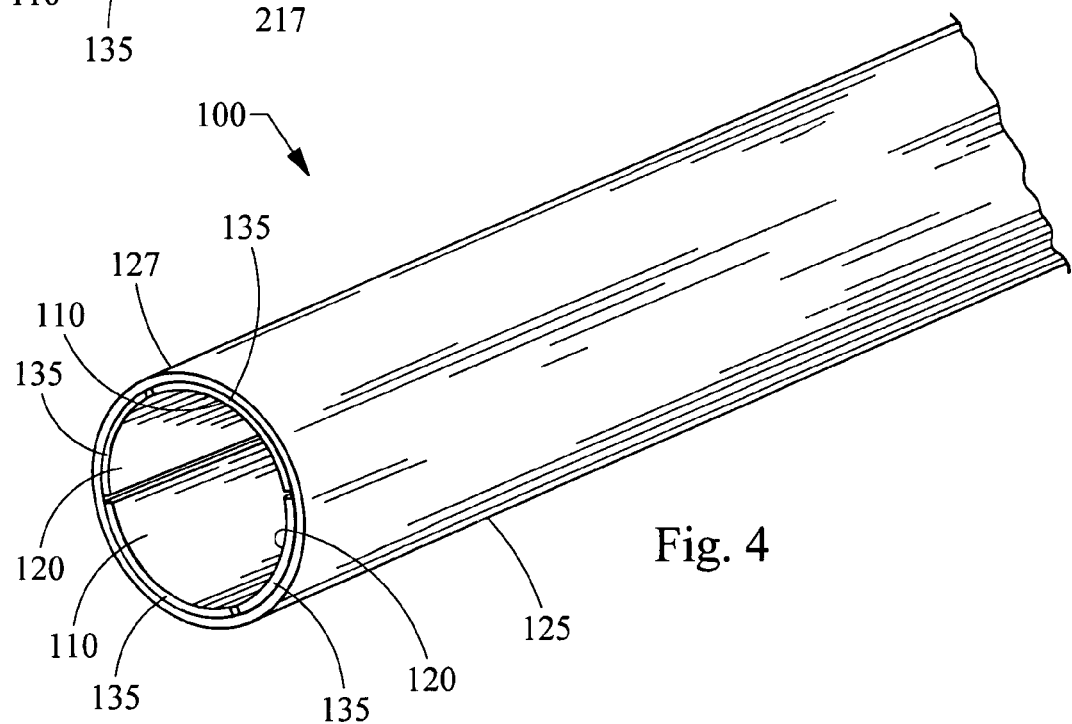
FIG. 4 is a perspective view of a portion of a deployment system according to another embodiment.

Referring to FIG. 4, a deployment system 100 including the first and second tubular sheaths 105, 115 may further comprise a third tubular sheath 125 overlying the first and second tubular sheaths 105, 115. The third tubular sheath 125 also overlies at least a portion of the flaps 110, 120. Preferably, the third tubular sheath 125 does not include flaps extending from the distal end 127. A distal portion of the third tubular sheath 125 overlying the flaps 110, 120 has an annular cross-section.

Preferably, each of the one or more flaps 110, 120 has a length that is longer than the longitudinal portion of the stent that the flap 110, 120 is adapted to overlie. Each flap 110, 120 may be from about 10% to about 20% longer than the stent. For example, a flap configured to overlie a longitudinal portion of a stent of 50 mm in length may have a length in the range of from about 55 mm to about 60 mm. A flap configured to overlie a longitudinal portion of a stent of 80 mm in length may have a length of from about 88 mm to about 96 cm. Because stents are available in a wide range of lengths, the length of the flaps may vary over a broad range. Generally, the flaps may have a length in the range of from about 20 mm to about 150 mm, although other lengths are possible. Preferably, the length of the flaps is in the range of from about 30 mm to about 90 mm.

Figure 5A:
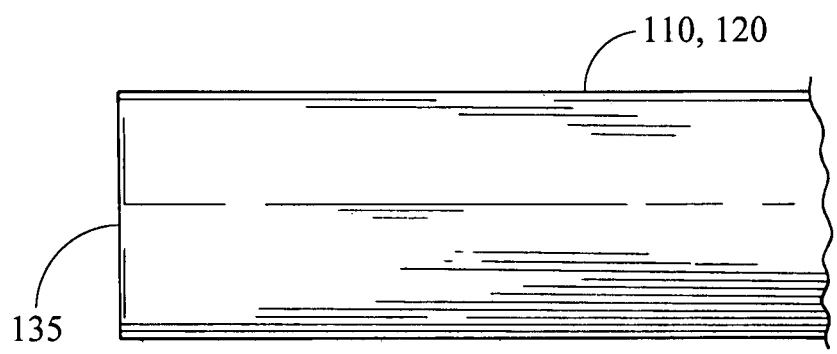
FIGS. 5A-5C are flattened plan views of a flap according to three embodiments showing different shapes of the flap.
Figure 5B:
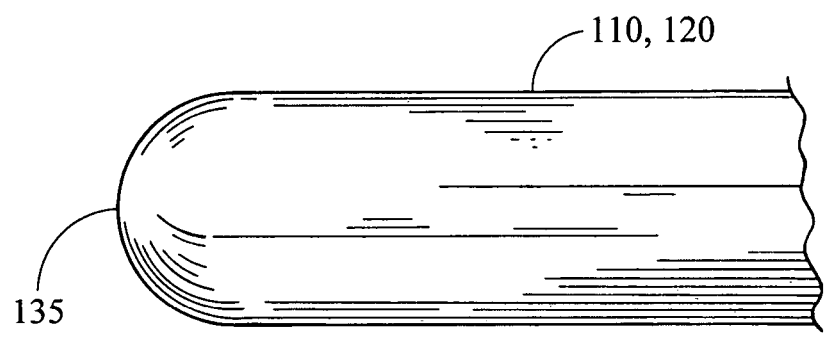
Figure 5C:
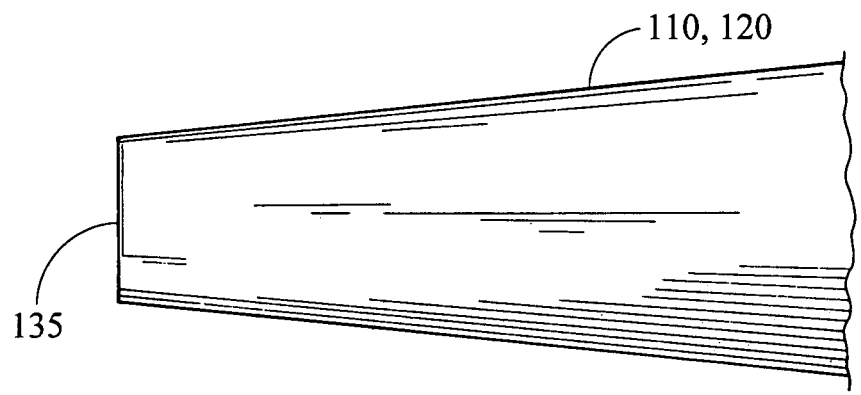

Preferably, the flaps 110, 120 have a rectangular shape in a flattened plan view, as shown for example in FIG. 5A. The distal portion 135 of the flaps may be curved, however, as shown for example in FIG. 5B. Other shapes of the one or more flaps are also possible and include, without limitation, trapezoidal (e.g., FIG. 5C), triangular, curved (e.g., S-shaped or hourglass-shaped), and angled (e.g., zigzig-shaped).

Including the length of any flaps, the tubular sheaths may have a total length ranging from about 50 cm (500 mm) to about 150 cm (1,500 mm). The tubular sheaths may be sized to fit a stent of any desired compressed diameter. Preferably, the tubular sheaths can accommodate stents having a compressed diameter in the range of from about 3 French to about 30 French.

Figure 6A:
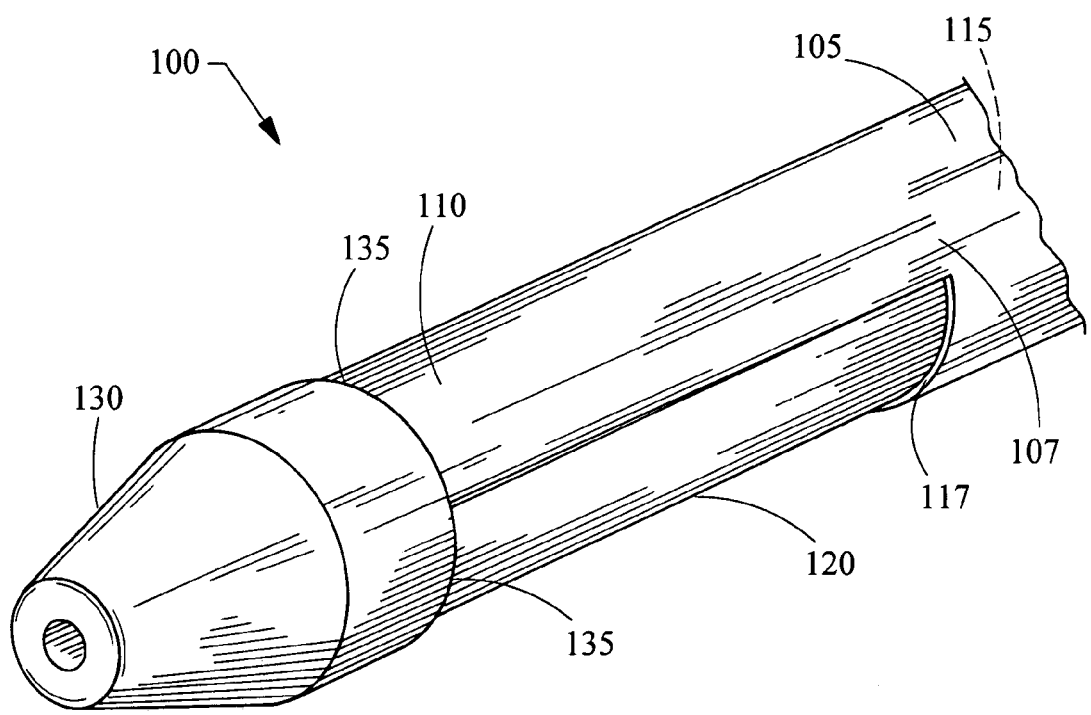
FIGS. 6A and 6B are perspective views of two embodiments of the deployment system including a distal cap.
Figure 6B:
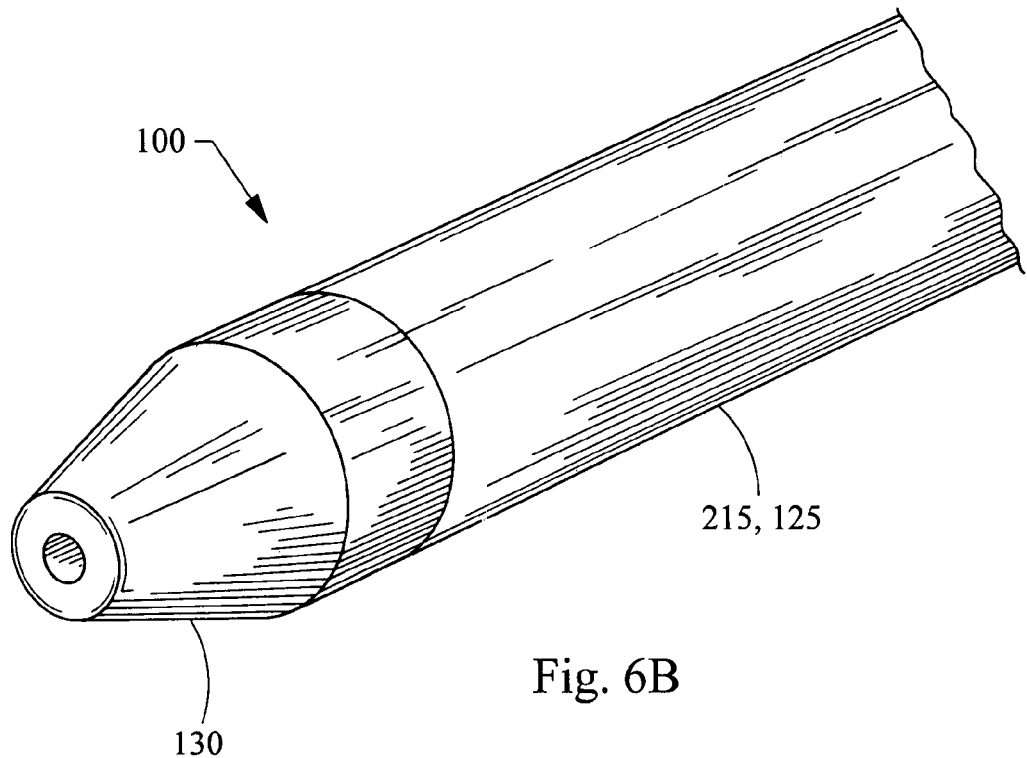

Referring to FIGS. 6A and 6B, the deployment system 100 may further include a distal cap 130 overlying a distal portion 135 of each of the one or more flaps 110, 120. The distal cap 130 preferably secures the distal portion 135 of each flap 110, 120 in place prior to expansion of the respective longitudinal portions of the stent. The distal cap 130 may also be used when the delivery system 100 includes only the first tubular sheath 105 having the one or more flaps 110.

In the following, the term "tubular sheath" is applicable to any of the first, second, and third tubular sheaths 105, 115, 215, and 125 described previously, and the terms "one or more flaps" or "flaps" are applicable to either the one or more flaps 110 of the first tubular sheath 105 or to the one or more flaps 120 of the second tubular sheath 115.

The tubular sheath and the one or more flaps are preferably made of a biocompatible material. The biocompatible material may include one or more polymers that can be processed by extrusion. The biocompatible material may be, for example, a polyamide (e.g., nylon), thermoplastic fluorocarbon (e.g., fluoroethylene-propylene (FEP)), polyether block amide (PEBA), polyolefin, polyimide, polyurethane, or polyvinyl chloride (PVC).

Preferably, a tubular sheath including one or more flaps is integrally formed from a single tubular preform. According to one embodiment, the tubular preform is formed by extrusion of the biocompatible material into a tube using conventional extrusion equipment known in the art. Alternatively, the tubular preform may be obtained from a single sheet of biocompatible material that has been bonded together along opposing edges to form a tube. Following the formation of the tubular preform, the one or more flaps may be cut from the preform using a blade, laser, or other cutting tool.

Alternatively, the tubular sheath and the one or more flaps may not be integrally formed from a single tubular preform. For example, the tubular sheath may be formed as described above, and the flaps may be cut from a sheet or another extruded tube. Then, the one or more flaps may be secured to the tubular sheath by, for example, adhesive bonding, solvent bonding, or thermal bonding.

The tubular sheath and/or the one or more flaps may include a reinforcement structure to improve the performance of the deployment system. The reinforcement structure of the sheath or flaps may be one or more wires, such as a flat wire or a round wire, according to one embodiment. The wire may be straight, bent, curved, coiled, or interwoven with other wires in a mesh, braid, or lattice. The reinforcement structure of the flaps may increase the stiffness and rigidity of the flaps and help to prevent premature deployment of the longitudinal portions of the stent. The reinforcement structure may further allow the flaps to adopt a particular desired shape. The reinforcement structure of the tubular sheath may enhance the pushability of the deployment system during delivery to the treatment site.

Figure 7A:
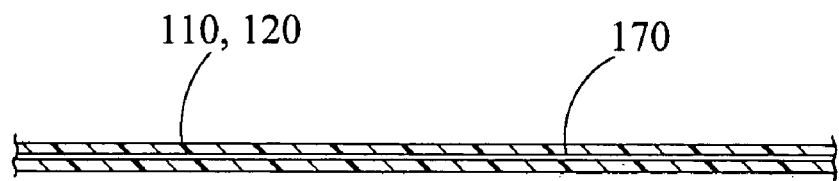
FIG. 7A is a longitudinal cross-sectional view of a portion of a flap showing an embedded reinforcement structure according to one embodiment.
Figure 7B:
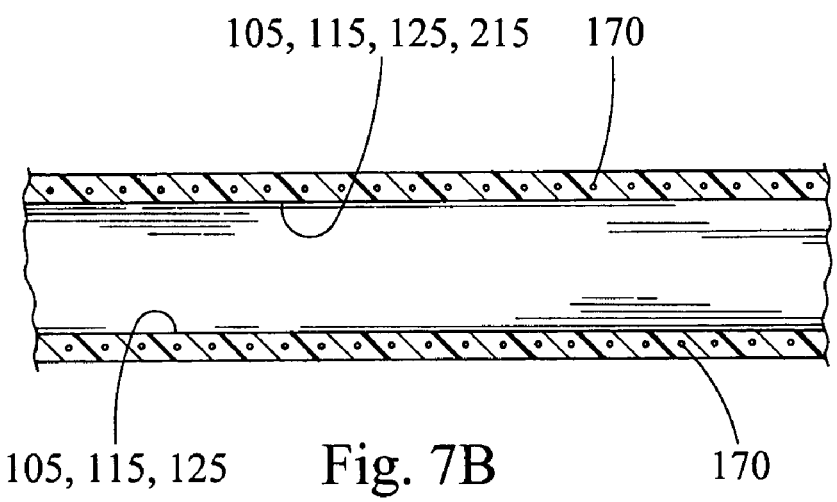
FIG. 7B is a longitudinal cross-sectional view of a portion of a tubular sheath showing an embedded reinforcement structure according to one embodiment.

According to one embodiment, the tubular sheath includes a reinforcement structure, and the flaps do not. Alternatively, the flaps may include a reinforcement structure and the tubular sheath may not. Preferably, each of the tubular sheath and the one or more flaps includes a reinforcement structure. The tubular sheath may have a different reinforcement structure from the one or more flaps. For example, referring to FIG. 7A, a longitudinally oriented wire may be preferred as the reinforcement structure 170 for each of the one or more flaps 110, 120, while it may be advantageous to provide the tubular sheath 105, 115, 125 with a helically wound wire as the reinforcement structure 170, as shown in FIG. 7B. Alternatively, a wire bent into a particular shape may be used to reinforce each of the one or more flaps. There may be overlap between the reinforcement structure of the tubular sheath and the reinforcement structure of the flaps. For example, the longitudinally oriented wires that may reinforce the flaps, as mentioned above, may extend longitudinally some distance into the tubular sheath.

It may be advantageous to at least partially embed the reinforcement structure(s) in a wall of the tubular sheath and/or a wall of the flaps. Preferably, a reinforcement structure 170 for the tubular sheath is completely embedded within the wall of the sheath, as shown for example in FIG. 7B, and a reinforcement structure for the flaps is completely embedded within the wall of the flaps, as shown for example in FIG. 7A.

The embedding of the reinforcement structure into the tubular sheath and/or flaps may be carried out during the processing of the tubular preform. It is preferable that the reinforcement structure be included in the tubular preform prior to forming the one or more flaps. For example, one or more reinforcement structures may be embedded in the tubular preform via bonding methods known in the art. An inner tubular preform may be slid onto a mandrel and the reinforcement structure(s) may be slid, wound, or otherwise disposed about the tubular preform. An outer tubular preform may then be applied over the reinforcement structure(s), and heat may be applied to bond the outer tubular preform to the inner tubular preform through gaps in or around the reinforcement structures. Alternatively, if the preform is extruded, it may be possible to incorporate the one or more reinforcement structures into the tubular preform during the extrusion process.

The reinforcement structure may be formed of any suitable material that may provide structural reinforcement, such as, for example, stainless steel, nickel-titanium alloys, or other metals, alloys, polymers, or composite materials that are either biocompatible or capable of being made biocompatible.

Figure 8:
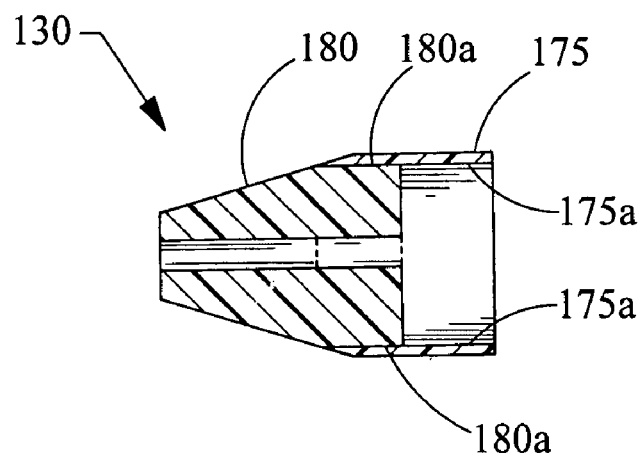
FIG. 8 is a sectional view of the distal cap according to one embodiment.

The distal cap 130 shown in FIGS. 6A and 6B may be fabricated by extrusion, molding, and/or bonding techniques known in the art. Referring to FIG. 8, for example, a tapered outer tube 175 having a small wall thickness may be coaxially disposed about a tapered inner tube 180 having a larger wall thickness. An inner surface 175a of the outer tube 175 may then be bonded to an outer surface 180a of the inner tube 180 using heat, adhesives, or solvents to form the distal cap 130. Preferably, the distal cap 130 is formed of one or more biocompatible materials, such as one or more biocompatible polymers. Examples of suitable polymers include, without limitation, polyamide (e.g., nylon), thermoplastic fluorocarbon (e.g., fluoroethylene-propylene (FEP)), polyether block amide (PEBA), polyolefin, polyimide, polyurethane, and polyvinyl chloride (PVC).

A method of deploying an expandable stent will now be described. The method includes radially expanding one or more longitudinal portions of an expandable stent in a first step to partially deploy the stent, and then radially expanding one or more other longitudinal portions of the stent in a second step to fully deploy the stent. Preferably, the expandable stent is a self-expanding stent, although the method may also be carried out using a balloon-expandable stent.

Figure 9:
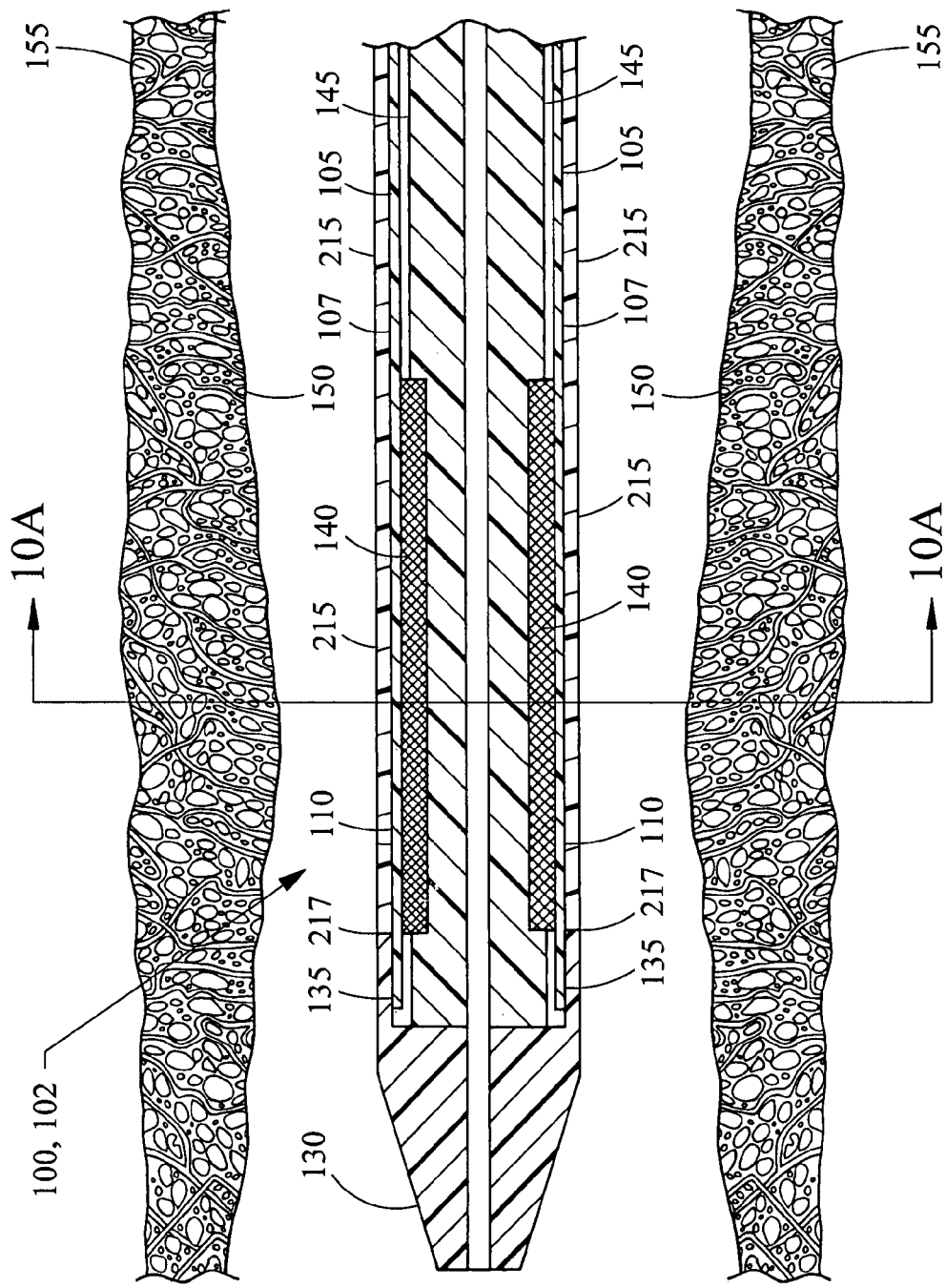
FIG. 9 is a longitudinal cross-sectional view of a distal part of the deployment system according to one embodiment prior to deployment of a stent.

Referring to FIGS. 9 and 10A to 12B, the deployment method is described below according to one embodiment of the deployment system 100. FIG. 9 is a sectional side view of a distal end 101 of the deployment system 100 including first and second tubular sheaths 105 and 215 prior to deployment of the stent. FIGS. 10A and 10B also show the deployment system 100 prior to deployment of a stent 140 (FIG. 10A is the cross-sectional view corresponding to FIG. 9). FIGS. 11A and 11B show the deployment system 100 following partial deployment of the stent 140, and FIGS. 12A and 12B show the deployment system 100 following complete deployment of the stent 140. FIGS. 10A, 11A, and 12A show the distal end 101 of the deployment system 100, while FIGS. 10B, 11B, and 12B show the proximal end 102.

Referring to FIG. 9 and FIG. 10A, the deployment system 100 includes a first tubular sheath 105 comprising two flaps 110 extending from a distal end 107 thereof, and a second tubular sheath 215 disposed coaxially with the first tubular sheath 105. The second tubular sheath 215 overlies the first tubular sheath 105 and the flaps 110, according to this embodiment. The two flaps 110 are disposed in opposition to each other and overlie longitudinal portions of an expandable stent 140 prior to deployment. Preferably, the expandable stent 140 is a self-expanding stent made of a superelastic material, such as a near-equiatomic nickel-titanium alloy (e.g., Nitinol).

Prior to delivery into a vessel 155, the stent 140 is placed over an inner catheter 145 and radially compressed to a low profile configuration. The radial compression may be carried out using commercially available stent crimping equipment. Once the stent 140 is in the low profile configuration, it may be transferred into a transfer tube or directly into the coaxially-disposed first and second tubular sheaths 105, 215. Preferably, a distal cap 130 overlies a distal portion 135 of each of the flaps 110 of the first tubular sheath 105. The distal cap 130 may be secured to the inner catheter 145 by any conventional means, such as, for example, a thermal bond, an adhesive bond, a threaded coupling, or an interference fit. It may also be possible for the distal cap 130 to be formed integrally with the inner catheter 145. It is preferable that the stent 140 is disposed proximal to but not underlying the distal cap 130 of the deployment system 100 so that longitudinal portions of the stent 140 may radially expand without obstruction upon retraction of the tubular sheaths 105, 215.

The method includes directing the deployment system 100 to a treatment site 150 in a body vessel 155 according to methods known in the art, as described previously. For example, a hollow needle may be used to penetrate the vessel and a wire guide may be threaded through the needle into the vessel. The needle may be removed, and an introduction catheter may be inserted over the wire guide. The deployment system 100 may then be advanced in a distal direction through the introduction catheter and into the vessel 155 to reach a treatment site 150, as shown in FIGS. 9 and 10A.

Referring to FIG. 10B, the second tubular sheath 215 is preferably attached to a handle, connector, Tuohy-Borst adapter, or another manipulator (collectively, "manipulator 165") disposed external to a patient at the proximal end 102 of the deployment system 100. The manipulator 165 facilitates manual retraction of the second tubular sheath 215 by a clinician. Similarly, the first tubular sheath 105 is preferably attached to a handle, connector, Tuohy-Borst adapter, or another manipulator (collectively, "manipulator 160") disposed external to the patient at the proximal end 102 of the deployment system 100. The manipulator 160 facilitates manual retraction of the first tubular sheath 105 by the clinician.

Preferably, the second tubular sheath 215 may be moved independently of the first tubular sheath 105 and the inner catheter 145. It is also preferable that the first tubular sheath 105 may be moved independently of the inner catheter 145 and the second tubular sheath 215. However, when the first tubular sheath 105 is retracted in a proximal direction, as discussed below, the second tubular sheath 215 may also be retracted.

The deployment system 100 may further include radiopaque markers on various internal components, such as, for example, the stent 140, the tubular sheaths 105, 215, the flaps 110, and the inner catheter 145. During the deployment procedure, the clinician may observe the impact of his or her external maneuverings on the intraluminal environment by using x-ray fluoroscopy, which illuminates the radiopaque markers.

Referring to FIGS. 11A to 11B, after the deployment system 100 is positioned at the treatment site 150, the second tubular sheath 215 may be retracted in a proximal direction to partially deploy the stent 140. As the second tubular sheath 215 is retracted, longitudinal portions of the stent 140 that do not underlie the two flaps 110 of the first tubular sheath 105 may radially expand and contact the vessel wall. The longitudinal portions of the stent 140 underlying the two flaps 110 of the first tubular sheath 105 are not deployed at this time, and the stent 140 is thus partially expanded.

If, as shown in FIG. 10A, the second tubular sheath 215 does not include flaps, then the sheath 215 is retracted to a position where the distal end 217 of the sheath 215 is proximal of the stent 140 to carry out the partial expansion. If the second tubular sheath 115 includes flaps 120, however, as shown for example in FIG. 2A, the sheath 115 is retracted to a position where the distal portion 135 of the flaps 120 is proximal of the stent 140.

Referring to FIG. 11A, the stent 140 may have a generally elliptical cross-section when partially deployed. Other cross-sectional shapes of the partially expanded stent 140 are also possible depending on the number and configuration of the flaps 110. Preferably, the cross-section of the stent 140 following partial deployment does not match a cross-section of the vessel 155.

Because one or more longitudinal portions of the stent 140 remain restrained by the delivery system 100 during retraction of the second tubular sheath 215, axial stretching and other deformation of the stent 140 may be minimized or avoided altogether as the stent partially deploys (radially expands).

Next, as shown in FIGS. 12A and 12B, the first tubular sheath 105 is retracted in a proximal direction. Accordingly, the longitudinal portions of the stent 140 disposed under the two flaps 110 of the first tubular sheath 105 during delivery are free to radially expand. As the expansion occurs and the first tubular sheath 105 is further retracted, the longitudinal portions of the stent 140 that are already engaged with the wall of the vessel 155 along the length of the stent 140 preferably prevent the stent 140 from stretching and twisting. Once the first tubular sheath 105 is retracted to a position where the distal portion 135 of the flaps 110 is proximal of the stent 140, the stent 140 expands to a fully deployed configuration in the vessel 155.

The deployment method described above in which the stent is radially expanded partially in a first step and then radially expanded fully in a second step may be carried out with other embodiments of the deployment system. For example, the deployment system of FIG. 4, which includes first, second, and third tubular sheaths, may be employed in the method, as described below in reference to FIG. 13 and FIGS. 14A to 17B.

Figure 13:
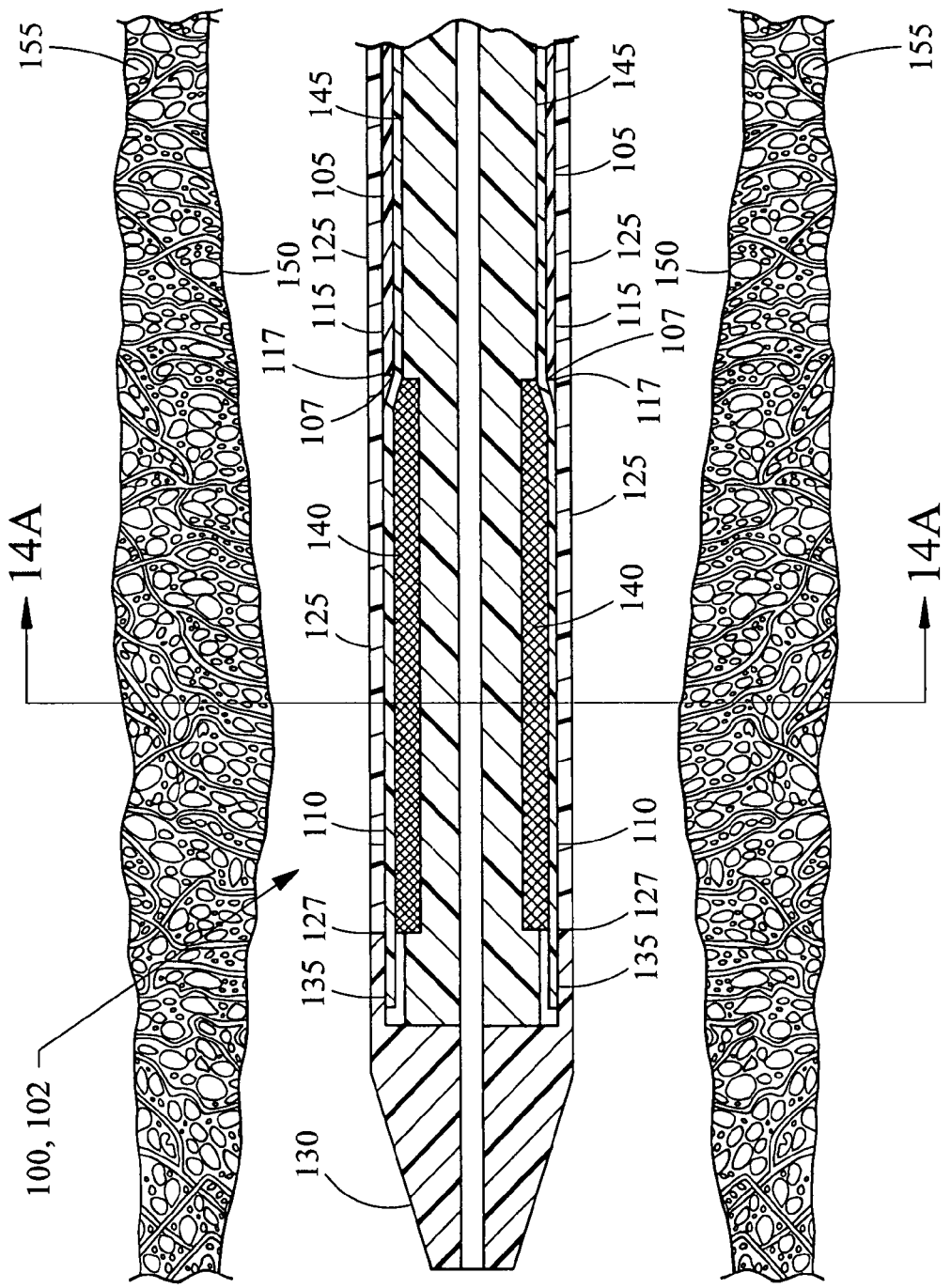
FIG. 13 is a longitudinal cross-sectional view of a distal part of the deployment system according to another embodiment prior to deployment of a stent.
Figure 14A:
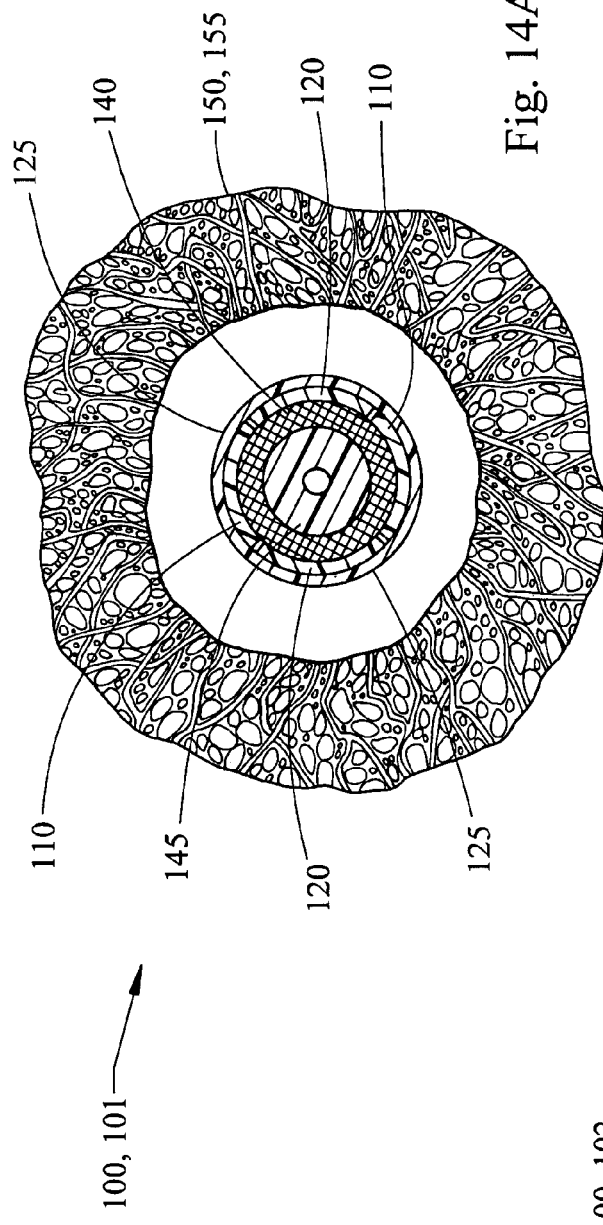
FIG. 14A is a cross-sectional view of the distal part of the deployment system shown in FIG. 13 taken along section 14A-14A.

FIG. 13 is a sectional side view of a distal end 101 of a deployment system 100 including first, second, and third tubular sheaths 105, 115, 125 prior to deployment of a stent 140. FIGS. 14A to 14B and FIGS. 15A to 15B also show the deployment system 100 prior to deployment of the stent 140 (FIG. 14A is the cross-sectional view corresponding to FIG. 13). FIGS. 16A and 16B show the deployment system 100 following partial deployment of the stent 140, and FIGS. 17A and 17B show the deployment system 100 following complete deployment of the stent 140. FIGS. 14A, 15A, 16A, and 17A show the distal end 101 of the deployment system 100, while FIGS. 14B, 15B, 16B, and 17B show the proximal end 102.

Referring to FIGS. 13 and 14A, the deployment system 100 includes a first tubular sheath 105 comprising two flaps 110 extending from a distal end 107 thereof, a second tubular sheath 115 comprising two flaps 120 (shown in FIG. 4) disposed coaxially with the first tubular sheath 105, and a third tubular sheath 125 overlying the first and second tubular sheaths 105, 115. The third tubular sheath 125 also overlies the flaps 110, 120 and thus may help to secure the flaps 110, 120 in positions overlying the longitudinal portions of the stent 140 as the deployment system 100 is being advanced through the vessel 155. Preferably, the expandable stent 140 is a self-expanding stent made of a superelastic material, such as a near-equiatomic nickel-titanium alloy (e.g., Nitinol).

Prior to delivery into a vessel 155, the stent 140 is placed over an inner catheter 145 and radially compressed to a low profile configuration, as described above. Once the stent 140 is in the low profile configuration, it may be transferred into a transfer tube or directly into the coaxially-disposed first, second and third tubular sheaths 105, 115, 125. Preferably, a distal cap 130 overlies a distal portion 135 of each of the flaps 110, 120 of the first and second tubular sheaths 105. The distal cap 130 may be secured to the inner catheter 145 by any conventional means, such as, for example, a thermal bond, an adhesive bond, a threaded coupling, or an interference fit. It may also be possible for the distal cap 130 to be formed integrally with the inner catheter 145. It is preferable that the stent 140 is disposed proximal to but not underlying the distal cap 130 of the deployment system 100 so that longitudinal portions of the stent 140 may deploy without obstruction upon retraction of the tubular sheaths 105, 115.

Figure 14B:
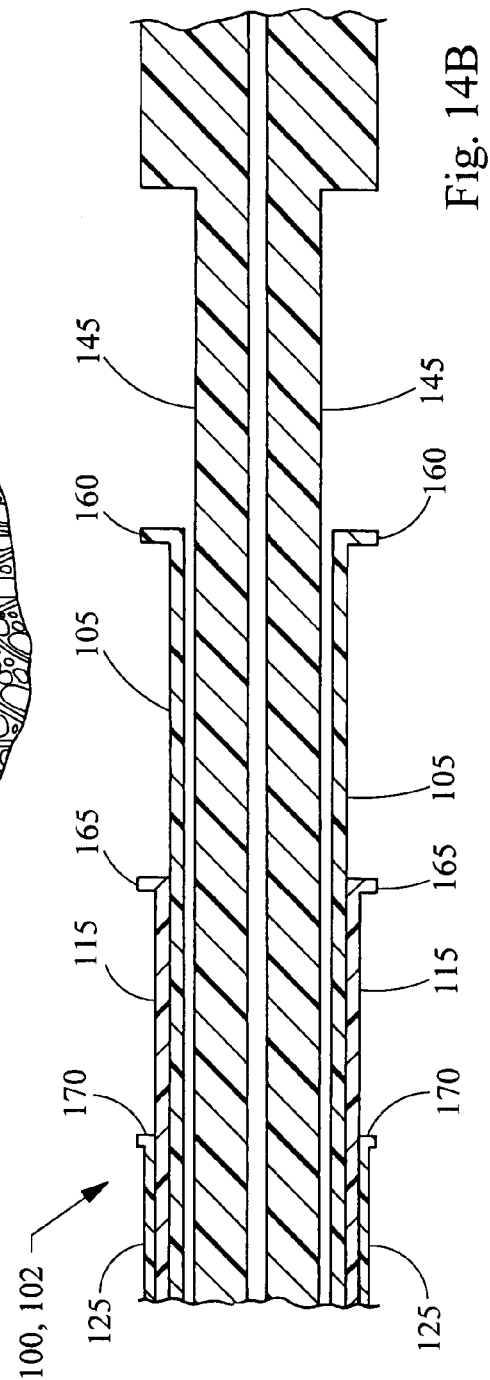
FIG. 14B is a longitudinal cross-sectional view of a proximal part of the deployment system of FIG. 13 prior to deployment of the stent.

Referring to FIG. 14B, the third tubular sheath 125 is attached to a handle, connector, Tuohy-Borst adapter, or another manipulator (collectively, "manipulator 170") disposed external to a patient at the proximal end 102 of the deployment system 100. The manipulator 170 facilitates manual retraction of the third tubular sheath 125 by a clinician. Similarly, the second tubular sheath 115 is attached to a handle, connector, Tuohy-Borst adapter, or another manipulator (collectively, "manipulator 165") disposed external to the patient at the proximal end 102 of the deployment system 100, and the first tubular sheath 105 is attached to a handle, connector, Tuohy-Borst adapter, or another manipulator (collectively, "manipulator 160") disposed external to the patient at the proximal end 102 of the deployment system 100. The manipulators 160, 165 facilitate manual retraction of the first and second tubular sheaths 105, 115 by the clinician.

Preferably, each of the tubular sheaths 105, 115, 125 may be moved independently of each other and of the inner catheter 145. However, when the second tubular sheath 115 is retracted in a proximal direction, the third tubular sheath 125 may also be retracted. Similarly, when the first tubular sheath 105 is retracted in a proximal direction, the second tubular sheath 115 and/or the third tubular sheath 125 may also be retracted.

The deployment system 100 may further include radiopaque markers on various internal components, such as, for example, the stent 140, the tubular sheaths 105, 115, 125, the flaps 110, 120, and the inner catheter 145. During the deployment procedure, the clinician may observe the impact of his or her external maneuverings on the intraluminal environment by using x-ray fluoroscopy, which illuminates the radiopaque markers.

The method includes directing the deployment system 100 to a treatment site 150 in a body vessel 155 according to methods known in the art, as described previously. Once the deployment system has reached the treatment site 150, the third tubular sheath 125 may be retracted. Preferably, upon retraction of the third tubular sheath 125, the longitudinal portions of the stent 140 underlying the first and second tubular sheaths 105, 115 remain unexpanded, as shown in FIGS. 15A and 15B. Then, the deployment method may proceed as described previously with the retraction of the second tubular sheath 115 to partially deploy the stent 140, and then the retraction of the first tubular sheath 105 to fully deploy the stent 140.

In particular, referring to FIGS. 16A and 16B, the second tubular sheath 115 may be retracted in a proximal direction to partially deploy the stent 140. As the second tubular sheath 115 is retracted, longitudinal portions of the stent 140 that do not underlie the two flaps 110 of the first tubular sheath 105 may radially expand and contact the vessel wall. The longitudinal portions of the stent 140 underlying the two flaps 110 of the first tubular sheath 105 are not deployed at this time. The sheath 115 is retracted to a position where the distal portion 135 of the flaps 120 is proximal of the stent 140, and the stent 140 is thus partially expanded.

Referring to FIG. 16A, the stent 140 may have a generally elliptical cross-section when partially deployed. Other cross-sectional shapes of the partially expanded stent 140 are also possible depending on the number and configuration of the flaps 110. Preferably, the cross-section of the stent 140 following partial deployment does not match a cross-section of the vessel 155.

Because one or more longitudinal portions of the stent 140 remain restrained by the delivery system 100 during retraction of the second tubular sheath 115, axial stretching and other deformation of the stent 140 may be minimized or avoided altogether as the stent partially deploys (radially expands).

Next, as shown in FIGS. 17A and 17B, the first tubular sheath 105 is retracted in a proximal direction. Accordingly, the longitudinal portions of the stent 140 disposed under the two flaps 110 of the first tubular sheath 105 during delivery are free to radially expand. As the expansion occurs and the first tubular sheath 105 is further retracted, the longitudinal portions of the stent 140 that are already engaged with the wall of the vessel 155 preferably prevent the stent 140 from stretching and twisting. Once the first tubular sheath 105 is retracted to a position where the distal portion 135 of the flaps 110 is proximal of the stent 140, the stent 140 expands to a fully deployed configuration in the vessel 155.

A method of deploying an expandable stent has been described. By carrying out the deployment of the stent in a multiple step process involving radial expansion of one or more longitudinal portions of the stent in one step and radial expansion of one or more other longitudinal portions in another step, it may be possible to minimize or eliminate axial stretching and twisting of the stent during deployment. Other advantages are also possible.

A deployment system for an expandable stent has also been described. The deployment system includes a first tubular sheath comprising one or more flaps extending from a distal end thereof. The flaps are configured to overlie one or more longitudinal portions of an expandable stent prior to expansion thereof. Preferably, the deployment system further includes a second tubular sheath disposed coaxially with the first tubular sheath. As described above, the deployment system may be advantageously employed to minimize unwanted deformation during expansion of an expandable stent.

Although the present invention has been described with reference to certain embodiments thereof, other embodiments are possible without departing from the present invention. The spirit and scope of the appended claims should not be limited, therefore, to the description of the preferred embodiments contained herein. All devices and methods that come within the meaning of the claims, either literally or by equivalence, are intended to be embraced therein. Furthermore, the advantages described above are not necessarily the only advantages of the invention, and it is not necessarily expected that all of the described advantages will be achieved with every embodiment of the invention.

What is claimed is:

1. A deployment system for an expandable stent comprising:
    an expandable stent in an unexpanded state;

a first tubular sheath comprising one or more first flaps extending from a distal end thereof, wherein the one or more first flaps overlie one or more first longitudinal portions of the stent, and further comprising a second tubular sheath overlying the first tubular sheath, the second tubular sheath including one or more second flaps extending from a distal end thereof, the one or more second flaps overlying one or more second longitudinal portions of the stent and being disposed alternately with the first flaps in a circumferential direction.

2. The deployment system of claim 1, wherein each of the one or more first flaps has a length at least as long as a length of the stent, and wherein each of the one or more first longitudinal portions extends entirely along the length of the stent but only partway about a circumference thereof.

3. The deployment system of claim 1, wherein each of the one or more first flaps has a length in the range of from about 20 mm to about 150 mm.

4. The deployment system of claim 1, wherein each of the one or more first flaps includes a reinforcement structure at least partially embedded therein.

5. The deployment system of claim 1, wherein the first tubular sheath comprises two first flaps disposed in opposition to each other.

6. The deployment system of claim 1, further comprising a distal cap overlying a distal portion of the one or more first flaps.

7. The deployment system of claim 1, wherein each of the one or more second flaps has a length in the range of from about 20 mm to about 150 mm.

8. The deployment system of claim 1, wherein each of the one or more second flaps includes a reinforcement structure at least partially embedded therein.

9. The deployment system of claim 1, wherein the second tubular sheath comprises two second flaps disposed in opposition to each other.

10. The deployment system of claim 1, further comprising a third tubular sheath overlying the second tubular sheath, wherein a distal portion of the third tubular sheath overlying the one or more first flaps and the one or more second flaps comprises an annular cross-section.

11. The deployment system of claim 1, wherein a distal cap overlies a distal portion of the one or more second flaps.

12. The deployment system of claim 1, wherein the first tubular sheath comprises two first flaps disposed in opposition to each other, the first flaps having a length in the range of from about 20 mm to about 150 mm and including a reinforcement structure at least partially embedded therein, and further comprising a distal cap overlying a distal portion of the two first flaps.

13. The deployment system of claim 12, wherein the second tubular sheath comprises two second flaps extending from a distal end thereof and overlying two second longitudinal portions of the stent, the two second flaps having a length in the range of from about 20 mm to about 150 mm and including a reinforcement structure at least partially embedded therein, wherein the two second flaps are disposed in opposition to each other and disposed alternately with the two first flaps in a circumferential direction, and further comprising a third tubular sheath overlying the second tubular sheath, wherein a distal portion of the third tubular sheath overlying the one or more first flaps and the one or more second flaps comprises an annular cross-section, and wherein the distal cap overlies a distal portion of the two second flaps.

* * * * *